United States Patent [19]

Burke et al.

[11] Patent Number: 5,723,301

[45] Date of Patent: Mar. 3, 1998

[54] METHOD TO SCREEN COMPOUNDS THAT AFFECT GAPDH BINDING TO POLYGLUTAMINE

[75] Inventors: James R. Burke, Chapel Hill; Jeffery M. Vance, Durham; Jan Enghild, Durham; Warren J. Strittmatter, Durham, all of N.C.

[73] Assignee: Duke University, Durham, N.C.

[21] Appl. No.: 553,110

[22] Filed: Nov. 3, 1995

[51] Int. Cl.$^6$ .................................................. G01N 33/68
[52] U.S. Cl. ............................................................ 435/7.1
[58] Field of Search ................................... 435/7.1, 7.8

[56] References Cited

PUBLICATIONS

Y.S. Jou et al.; Evidence from antibody studies that the CAG repeat in the Huntington disease gene is expressed in the protein, *Hum. Molec. Genet.* 4:465–469 (1995).

I. Yazawa et al.; Abnormal gene product identified in hereditary dentatorubral–pallidoluysian atrophy (DRPLA) brain, *Nature Genet.* 10:99–103 (1995).

P.J. Willems et al.; Dynamic mutations his double figures, *Nature Genet.* 8:213–215 (1994).

O. Onodera et al.; Molecular Cloning of a Full–length cDNA for Dentatorubral–Pallidoluysian Atrophy and Regional Expressions of the Expanded Alleles in the CNS, *Am. J. Hum. Genet.* 57:1050 1995).

A.R. LaSpada et al.; Meiotic stability and genotype–phenotype correlation of the trinucleotide repeat in X–linked spinal and bulbar muscular atrophy, *Nature Genet.* 2:301–304 (1992).

R. Kodie et al.; Unstable expansion of CAG repeat in hereditary dentatorubral–pallidoluysian atrophy (DRPLA), *Nature Genet.* 6:9–13 (1994).

S. Nagafauchi et al.. Dentatorubral and pallidoluysian atrophy expansion of an unstable CAG trinucleotide on chromosome 12p, *Nature Genet.* 6;14–18 (1994).

Huntington's Disease Collaborative Research Group; A Novel Gene Containing a Trinucleotide Repeat That is Expanded and Unstable on Huntington's Disease Chromosomes, *Cell* 72:971–983 (1993).

Y. Kawaguchi et al.; CAG expansions in a novel gene for Machado–Joseph disease at chromosome 14q32.1, *Nature Genet.* 8:221–227) 1994).

Y. Trottier et al.; Cellular localization of the Huntington's disease protein and discrimination of the normal and mutated form, *Nature Genet.* 10:104–110 (1995).

M. DiFiglia et al.; Huntingtin is a Cytoplasmic Protein Associated with Besicles in Human and Rat Brain Neurons, *Neuron* 14:1075–1081 (1995).

A.H. Sharp et al.; Widespread Expression of Huntington's Disease Gene (IT15) Protein Product, *Neuron* 14:1065–1074 (1995).

A.T. Hoogeveen et al.; Characterization and Localization of the Huntington's disease gene product, *Hum. Mol. Genet.* 2:2069–2073 (1993).

M.F. Perutz et al.; Glutamine repeats as polar zippers: Their possible role in inherited neurodegenerative diseases, *Proc. Natl. Acad. Sci. U.S.A.* 91:5355–5358 (1994).

W.J. Strittmatter et al.; Binding of human apolipoprotein E to synthetic amyloid β peptide: Isoform–specific effects and implications for late–onset Alzheimer disease, *Proc. Natl. Acad. Sci. U.S.A.* 90:8098–8102 (1993).

R. Singh et al.; Sequence–Specific Binding of Transfer RNA by Glyceraldehyde–3–Phosphate Dehydrogenase, *Science* 259:365–368 (1993).

E. Nagy et al.; Glyceraldehyde–3–phosphate Dehydrogenases Selectively Binds AU–rich RNA in the NAD$^+$–binding Region (Rossman Fold), *Biol. Chem.* 270:2755–2763 (1995).

Lachaal et al.; An ATP–modulated Specific Association of Glyceraldehyde–3–phosphate Dehydrogenase with Human Erythrocyte Glocose Transporter, *J. Biol. Chem.* 265:15449–15454 (1990)

Burke et al.; The Haw River Syndrome: Dentatorubropallidoluysian atrophy (DRPLA) in an African–American family, *Nature Genet.* 7:521–524 (1994).

Mejean et al.; Antigenic probes binding sites for the glycolytic enzymes glyceraldehyde–3–phosphate dehydrogenase, aldolase and phosphofructokinase on the actin monomer in microfilaments, *Biochem J.* 264:671–677 (1989).

S. Nagafuchi et al.; Structure and expression of the gene responsible for the triplet repeat disorder, dentatorubral and pallidoluysian atrophy (DRPLA), *Nature Genet.* 8:177–182 (1994).

Morgenegg et al.; Glyceraldehyde–3–Phosphate Dehydrogenase Is a Nonhistone Protein Activator of Transcription in Neurons, *J. Neurochem.* 47:54–62 (1986).

LaSpada et al.; Trinucleotide Repeat Expansion In Neurological Disease, *Ann. Neurol.* 36:814–822 (1994).

Ranum et al.; Molecular and Clinical Correlations in Spinocerebellar Atazia Tupe I: Evidence for Familiarl Effects on the Age at Onset, *Am. J. Human. Genetics* 55:244–252 (1994).

O'Donovan et al.; Expanded CAG repeats in schizophrenia and bipolar disorder, *Nature Genet.* 10:380–381 (1995).

Housman Gain of Glutamines, gain of function?, *Nature Genet.* 10:3–4 (1995).

Landwehrmeyer et al.; Huntington's Disease Gene: Regional and Cellular Expression in Brain of Normal and Affected Individuals, *Am. Neurol. Assoc.* 37:218–230 (1995).

(List continued on next page.)

*Primary Examiner*—Marianne P. Allen
*Assistant Examiner*—Robert C. Hayes
*Attorney, Agent, or Firm*—Bell, Seltzer, Park & Gibson

[57] ABSTRACT

GAPDH binds to expanded polyglutamine regions which are found in proteins encoded by genes with CAG repeat domains, which genes cause inherited neurodegenerative disorders and are associated with certain psychiatric disorders. Therapeutic methods are based on inhibiting the binding of GAPDH to expanded polyglutamine regions. A method of screening compounds for the ability to inhibit binding of GAPDH to polyglutamine regions is described.

1 Claim, 5 Drawing Sheets

OTHER PUBLICATIONS

A. Roses; Alzheimer's Disease as a Model of Molecular Gerontology, *J. NIH Research* 7:51–56 (1995).

Verlinde et al.; Selective Inhibition of Trypanosomal Glyceraldehyde–3–phosphate Dehydrogenase by Protein Structure–Based Design: Toward New Drugs for the Treatment of Sleeping Sickness, *J. Medicinal Chemistry* 37:3605–3613 (1994).

Caskey et al.; Triplet Repeat Mutations in Human Disease, *Science* 256:784–789 (1992).

Gusella & MacDonald; Huntington's disease, *Seminars in Cell Biology* 6:21–28 (1995).

Somers et al.; Analysis of the binding of glyceraldehyde–3–phosphate dehydrogenase to microtubles, the mechanism of bundle formation and the linkage effect, *Eur. J. Biochem.* 193:437–444 (1990).

Van Tuinen et al.; Immunolocaliztion of Glyceraldehyde–3–Phosphate Dehydrogenase, Hexokinase, and Carboxypeptidase Y in Yeast Cells at the Ultrastructural Level, *J. Histochem. Cytochem.* 35:327–333 (1987).

S.E. Andrew et al.; The relationship between Trinucleotide (CAG) repeat length and clinical features of Huntington's Disease, *Nature Genet.* 4:389–403 (1993).

K. Meyer–Siegler et al.; A Human nuclear uracil DNA Glycosylase is the 37–kDa subunit of glyceraldehyde–3–phosphate dehydrogenase, *Proc. Natl. Acad. Sci. USA* 88:8460–8464 (1991).

METHOD TO SCREEN COMPOUNDS THAT AFFECT GAPDH BINDING TO POLYGLUTAMINE

This invention was made with Government support under grant number K08NS01533 from the National Institutes of Health. The Government has certain rights to this invention.

FIELD OF THE INVENTION

The present invention concerns methods of inhibiting binding of GAPDH to polyglutamine regions of proteins in cells, and methods of treating inherited neurodegenerative diseases which are caused by genes containing an expanded CAG repeat domain, by inhibiting the binding of GAPDH to polyglutamine regions of proteins in affected cells.

BACKGROUND OF THE INVENTION

At least six adult-onset neurodegenerative diseases are due to genes containing a variably increased CAG repeat within the coding region. La Spada et al., Ann Neurol 36:814 (1994). These include dentatorubral-pallidoluysian atrophy (DRPLA), Huntington's disease (HD), spinobulbar muscular atrophy (SBMA or Kennedy's disease), Machado-Joseph disease (MJD), spinocerebellar ataxia type 1 (SCA1), and the Haw River syndrome (HRS) (R. Koide et al., *Nature Genet.* 6:9-13 (1994); S. Nagafuchi et al., *Nature Genet.* 6:14-18 (1994); Huntington's Disease Collaborative Research Group, *Cell* 72:971-983 (1993); P. Willems, *Nature Genet.* 8:213-215 (1994) and Burke et al., *Nature Genet.* 7:521 (1994)). Additional neurodegenerative diseases may be found to be due to the presence of expanded CAG repeat domains as the genetic bases of such diseases are investigated further.

These diseases demonstrate similar properties including the phenotype of progressive dementia and movement disorders. Unaffected individuals have fewer than a minimum number of CAG repeats (generally fewer than 40) in the affected gene, while affected patients have more than this number of repeats (La Spada et al., *Ann. Neurol.* 36:814 (1994). The severity and age of onset of these diseases roughly correlate with the size of the inherited CAG repeat (R. Koide et al., *Nature Genet.* 6:9-13 (1994); S. Andrew et al., *Nature Genet.* 4:398-403 (1993); L. Ranum et al., *Am. J. Human Genet.* 55:244-252 (1994)). The presence of CAG repeats has also been implicated in certain psychiatric disorders (schizophrenia and bipolar disorder). O'Donovan et al., *Nature Genet.*, 10;380 (1995).

The CAG triplet repeat domain produces a polyglutamine domain in the expressed proteins (Huntington's Disease Collaborative Research Group, *Cell* 72:971-983 (1993); S. Nagafuchi et al., *Nature Genet.* 8:177-182 (1994); Y. Jou and R. Myers, *Human Molec. Genetics* 4:465-469 (1995)). All of these diseases (except X-linked spinobulbar muscular atrophy) are expressed as autosomal dominant traits.

SUMMARY OF THE INVENTION

The present invention is based on the finding that Glyceraldehyde-3-phosphate dehydrogenase (GAPDH) binds to expanded polyglutamine regions. Expanded polyglutamine regions are found in proteins encoded by genes with CAG repeat domains, which genes cause inherited neurodegenerative disorders. The present invention provides a method of inhibiting GAPDH binding to expanded polyglutamine regions, by administering to (or introducing into) an affected cell either an inhibitor of GAPDH binding to polyglutamine regions, or a substrate of GAPDH. Administration may be carried out by either delivering the active agent directly to the cell, or by delivering genetic material to the cell which in turn delivers the active agent to the cell.

A first aspect of the present invention is a method of treating a neurodegenerative disease caused by a gene containing an expanded CAG domain which is translated into a polyglutamine region. The treatment comprises administering a compound which inhibits binding of GAPDH to the polyglutamine region. The GAPDH inhibitor may be selected from GAPDH, fragments of GAPDH which bind to the polyglutamine region, and peptidomimetics or organomimetics of these inhibitors.

A further aspect of the present invention is a method of treating a neurodegenerative disease caused by a gene containing an expanded CAG domain which is translated into a polyglutamine region, comprising administering a GAPDH substrate.

A further aspect of the present invention is a method of treating a psychiatric disorder caused by a gene containing an expanded CAG domain which is translated into a polyglutamine region, comprising administering a compound which inhibits binding of GAPDH to the polyglutamine region.

A further aspect of the present invention is a method of treating a psychiatric disorder caused by a gene containing an expanded CAG domain which is translated into a polyglutamine region, comprising administering a GAPDH substrate.

A further aspect of the present invention is a method of screening compounds for the ability to inhibit binding of GAPDH to polyglutamine regions, comprising providing an aqueous solution containing a test compound, molecules having an expanded polyglutamine region, and GAPDH, and then detecting whether binding of GAPDH is reduced in the presence of the test compound.

A further aspect of the present invention is a method of inhibiting degeneration of a nerve cell, which nerve cell has a gene containing an expanded CAG domain which is translated into a polyglutamine region, the method comprising inhibiting the binding of GAPDH to the polyglutamine region.

The foregoing and other objects and aspects of the present invention are explained in detail in the drawings herein and the specification set forth below.

DETAILED DESCRIPTION OF THE INVENTION

Figure 1:
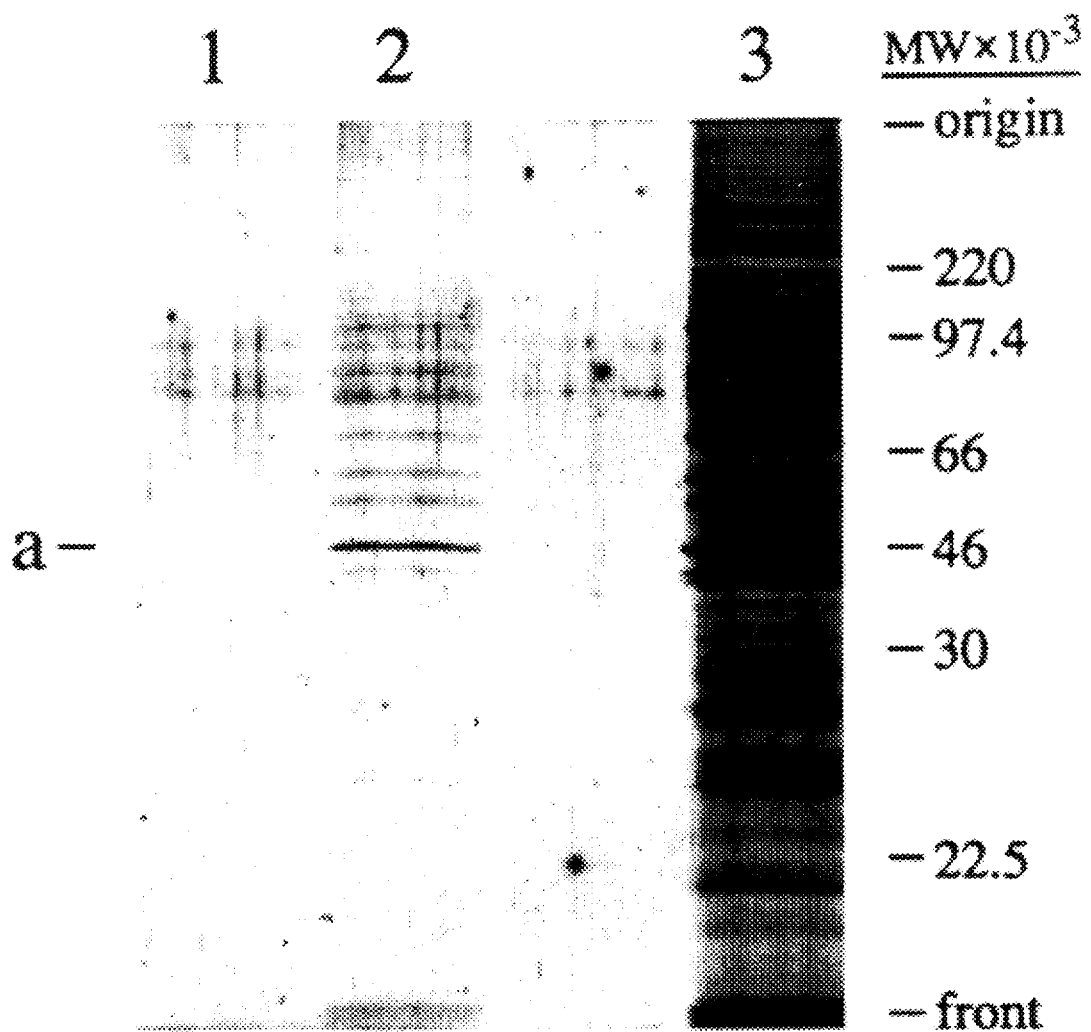
FIG. 1 shows a silver-stained SDS polyacrylamide gel demonstrating the binding of brain homogenate proteins to immobilized 20-glutamine peptide or 60-glutamine peptide. Lane 1 displays brain proteins eluted from 20-glutamine peptide with glycine; Lane 2 displays brain proteins eluted from 60-glutamine peptide with glycine; Lane 3 displays brain homogenate.

Amino acid and nucleotide sequences provided herein are presented in the amino to carboxy direction, from left to right. The amino and carboxy groups are not presented, and nucleotide sequences are presented in single strand only, in the 5' to 3' direction from left to right. Nucleotides and amino acids are represented herein in the manner recommended by the IUPAC-IUB Biochemical Nomenclature Commission, or (for amino acids) by three letter code, in accordance with 37 CFR §1.822 and established usage. See, e.g., PatentIn User Manual, 99–102 (November, 1990) (U.S. Patent and Trademark Office, Office of the Assistant Commissioner for Patents, Washington, D.C. 20231).

In HD, DRPLA, SBMA, MJD and SCA1 the expanded CAG domain is known to be located within an open reading frame of the gene (Housman, Nature Genetics 10:3 (1995); Willems, Nature Genetics 8:213 (1994); Kawaguchi et al., Nature Genetics 8:221 (1994)). It has been shown that the CAG domain encodes an expanded polyglutamine region in the expressed protein, and that this expression is necessary for associated neurodegenerative pathology in HD, DRPLA, and SCA1 (Housman, Nature Genetics 10:3 (1995); Nature Genetics, 10:94 (1995); Yazawa et al., Nature Genetics, 10:99 (1995); and Trottier et al., Nature Genetics 10:104 (1995)). In those studies, cells of affected patients were shown to contain an immunoreactive gene product of increased molecule weight in addition to the normal sized protein. The HD gene product (huntingtin) has an unknown function; the SBMA gene product (androgen receptor or AR) regulates transcription; the SCA1 polypeptide (ataxin) has an unknown function; and the DRPLA polypeptide also has an unknown function.

Each known CAG-domain neurodegenerative disease is associated with a unique gene and gene product, and has a specific pattern of degeneration and clinical phenotype. The selective neuronal degeneration seen in these disorders is not explained by the cellular distribution of the expressed proteins, since both the normal and mutant proteins are widely expressed throughout the central nervous system (I. Yazawa et al., Nature Genet. 10:99–103 (1995); Y. Trottier et al., Nat. Genet. 10:104–110 (1995); A. Hoogeveen et al., Hum. Mol. Genet. 2:2069–2073 (1993); G. Landwehrmeyer et al., Ann. Neurol. 37:218–230 (1995)). Additional factors such as alternative splicing, post-translational modifications and the presence of other cell-specific protein interactions are possible explanations of the selective cell vulnerability. An abnormal gain of function due to the expanded polyglutamine region in the expressed proteins has been postulated. La Spada et al., Ann. Neurol. 36:814 (1994); Housman, Nat. Genetics 10:3 (1995). Neurodegenerative diseases in addition to those listed above may be found to be due to the presence of expanded CAG repeat domains as the genetic bases of such diseases are investigated further.

The presence of genes containing CAG repeats has also been implicated in certain psychiatric disorders (schizophrenia and bipolar disorder). O'Donovan et al., Nature Genet., 10;380 (1995).

The association of CAG repeats with multiple adult-onset neurodegenerative diseases implies a common mechanism for the associated pathology. Any postulated common mechanism must fulfill several criteria. First, the polyglutamine domain must functionally regulate protein interactions; second, the size of the polyglutamine domain should quantitatively determine protein interactions; third, the expressed gene product must be co-localized with the protein in the affected cell for protein interactions to be physiologically relevant.

The present inventors sought to identify brain proteins which selectively interacted with polyglutamine-domain proteins, to determine if increased polyglutamine region size altered protein interactions to produce a novel pathogenetic mechanism common to CAG-domain diseases. The present data indicate that CAG associated neurodegenerative diseases share a metabolic pathogenesis involving GAPDH as a functional component.

The present inventors have found that GAPDH binds to synthetic peptides with expanded polyglutamine regions, as well as to DRPLA protein and huntingtin from unaffected individuals with normal sized polyglutamine domains. DRPLA and huntingtin may bind to GAPDH through the polyglutamine domain itself, or alternatively, this domain may secondarily alter another binding region. Synthetic polyglutamine peptides form β-sheets held together by hydrogen bonds which may function as polar zippers capable of binding proteins or nucleic acids (M. Perutz et al., Proc. Natl. Acad. Sci. USA 91:5355–5358 (1994)). A mechanism by which a polar zipper would cause cell death has not yet been established.

GAPDH has many enzymatic and binding activities. The two major enzymatic activities of GAPDH are in glycolysis/ gluconeogenesis and as a uracil DNA glycosylase (K. Meyer-Siegler et al., Proc. Natn. Acad. Sci. USA 88:8460–8464 (1991)). Other functions of GAPDH include binding tRNA (R. Singh and M. Green, *Science* 259:365–368 (1993)), AU-rich regions of RNA (E. Nagy and W. Rigby, *J. Biol. Chem.* 270:2755–2763 (1995)), ATP (A. Nakai et al., *Biochem. Biophys. Res. Commun.* 176: 59–64 (1991)), and calcyclin (F. Zeng et al., *Int. J. Biochem.* 25:1019–1027 (1993)). GAPDH forms complexes with the C-terminal region of the amyloid precursor protein (H. Schulze et al., *J. Neurochem.* 60:1915–1922 (1993)). GAPDH also binds the erythrocyte glucose transporter (M. Lachaal et al., *J. Biol. Chem.* 265:15449–15454 (1990)), actin (C. Mejean et al., *Biochem. J.* 264:671–677 (1989)) and tubulin (M. Somers et al., *J. Eur. J. Biochem.* 193:437–444 (1990)).

Data presented herein demonstrate selective differences between GAPDH binding to normal and abnormal sized polyglutamine regions. Peptides with expanded polyglutamine regions may have quantitatively different protein-protein interactions compared to peptides with smaller polyglutamine regions, binding with different kinetics or equilibria constants. Differences in mutant and native protein binding with GAPDH would affect the enzymatic or structural functions of GAPDH and, over years, subtle changes in neuronal function might lead to death of vulnerable neurons (see, e.g., A. Roses, *J. NIH Res.* 7:51–57 (1995)). Larger polyglutamine repeats are likely to have greater effects, consistent with the observation that patients with larger CAG repeats generally develop disease at earlier ages.

The interaction of polyglutamine regions with GAPDH could lead to neurodegeneration through several mechanisms. Polyglutamine may inhibit the function of GAPDH in glycolysis causing a chronic energy deficit, or could interfere with the role of GAPDH as a uracil DNA glycosylase resulting in impaired DNA repair, or disrupt binding of GAPDH to cytoskeletal elements such as tubulin, altering neuronal morphology, function and survival.

The gene products of Huntington's and DRPLA are predominantly cytoplasmic in nerve cells, with more recent evidence suggesting that huntingtin is associated with the cytoskeleton and membranes. I. Yazawa et al., *Nature Genet.* 10:99–103 (1995); Y. Trottier et al., *Nat. Genet.* 10:104–110 (1995); A. Sharp et al., *Neuron* 14:1065–1074 (1995); and M. DiFiglia et al., *Neuron* 14:1075–1081 (1995). One report states that huntingtin is found in the nucleus. A. Hoogeveen et al., *Hum. Mol. Genet.* 2:2069–2073 (1993). The SCA1 gene product (ataxin) is found in both the nucleus and the cytoplasm of Purkinje cells of the cerebellum, which degenerate in SCA1. Housman, *Nat. Genetics* 10:3 (1995). GAPDH is ubiquitous in the cell, with the major fraction in the cytoplasm associated with cytoskeletal proteins and membranes and small amounts in the nucleus. E. van Tuinen et al., *J. Histochem. Cytochem.* 35:327–333 (1987); G. Minaschek et al., *J. Eur. J. Cell Biol.* 58:418–428 (1992); Z. Ronai, *Inter. J. Biochem.* 25:1073–1076 (1993); G. Morgenegg et al., *Neurochem.* 47:54–62 (1986); H. Knull et al., *Comp. Biochem. Physiol.* [B] 81:349–351 (1985).

Impairment of cellular energy generation has long been considered a potential mechanism for pathogenesis in neurodegenerative diseases, especially Huntington's Disease. Beal, *Ann. Neurology* 31:119 (1992). Numerous studies of HD patients and those at risk have demonstrated decreased glucose utilization by positron emission tomography (PET) scan. Mazziota et al., *New Engl. J. Med.* 316:357 (1987); Grafton et al., *Arch. Neurol.* 49:1161 (1992); Kuwert et al. *Brain* 113:1405 (1990); Martin et al., *Neurology* 42:223 (1992); Kuhl et al., *Ann. Neurol.* 15 Suppl:S119–S125 (1984); Jenkins et al., *Neurology* 43:2689 (1993). Chronic defects in cellular energy metabolism have been postulated to cause neurodegeneration as a result of "weak excitotoxicity". See, e.g., Albin and Greenamyre, *Neurology,* 42:733 (1992); Beal, *Ann. Neurology* 31:119 (1992)). Brouillet et al., *Proc. Natl. Acad. Sci.* 92:7105 (1995) demonstrated that systemic administration of a metabolic toxin could exert focal destruction of specific populations of neurons in non-human primates. Neurons, because they are post-mitotic, long-lived and have high energy demand may be more susceptible to chronic energy depletion than other cell types.

In glycolysis, GAPDH functions primarily as a tetramer (Harris et al., Glyceraldehyde-3-phosphate dehydrogenase, In Boyer (Ed.), *The Enzymes,* Academic Press, New York, 1–49 (1976)) while the monomer is active as a uracil DNA glycosylase (Meyer-Siegler et al., *Proc. Natl. Acad. Sci.* 88:8460 (1991)) and in stimulation of tubulin polymerization (Durrieu et al. *Arch. Biochem Biophys.* 252:32 (1987)).

Chronic defects in DNA repair have been postulated as contributing to a number of neurodegenerative diseases. Rao, *Mol. Neurobiol.* 7:23 (1993); Mazzarello et al., *J. Neurol. Sci.* 112:4 (1992); Imray et al., *Mutation Research* 112:369 (1983); Moshell et al., *Lancet* 1:9 (1980); Scudiero et al., *Proc. Natl. Acad. Sci.* 78:6451 (1981); Beverstock et al., *Mutat. Res.* 96:75 (1982); Evans et al., *Ann. Hum. Genet.* 46:177 (1982). GAPDH was recently identified as identical to an enzyme that had been characterized as a uracil DNA glycosylase (UDG). Meyer-Siegler et al., *Proc. Natl. Acad. Sci. USA* 88:8460 (1991). UDG removes uracil when it occurs in DNA due to misincorporation of deoxyuridine triphosphate or from deamination of cytosine. It is estimated that spontaneous deamination occurs at a rate of 100–300 events/cell/day (Lindahl et al., *Biochemistry* 13:3405 (1974)), implying a continual need for UDG activity. If expanded polyglutamine domain proteins inhibit GAPDH-UDG activity, neurodegeneration could occur as a consequence. It is further possible that polyglutamine repeat protein binding prevents transport of GAPDH to the nucleus or that the GAPDH-repeat protein is transported but dysfunctional, and the amount of repeat protein in the nucleus too small to be detected immunohistochemically. Such pathways would explain how cytoplasmic proteins such as huntingtin and DRPLA interfere with nuclear based DNA repair proteins.

GAPDH promotes tubulin polymerization, the major constituent of microtubules. Somers et al., *European J. Biochem.* 193:437 (1990); Walsh et al., *Biochim. Biophys. Acta* 999:64 (1989); Muronetz et al., *Arch. Biochem Biophys.* 313:253 (1994). Modification of GAPDH stimulation of tubulin polymerization by expanded polyglutamine repeat proteins may result in aberrant control of the cytoskeleton and ultimately neuronal dysfunction and death.

GAPDH is widely distributed in the body but the pathology seen in polyglutamine repeat diseases is focal in nature. Further, in HD, DRPLA, SCA1 and SBMA both the mutant and normal allele are transcribed and translated widely throughout the brain and body. The brain may be the target in these five polyglutamine repeat diseases because neurons are post-mitotic cells susceptible to chronic accumulation of damage. This sensitivity of neurons compared to other cells,. is demonstrated by systemic administration of the succinate dehydrogenase inhibitor, 3-nitroproprionic acid, which causes specific destruction of striatal neurons. Brouillet et al., *Proc. Natl. Acad. Sci. USA* 92:7105 (1995).

The focal pathology seen in polyglutamine repeat disease may further be explained by lack of binding between GAPDH and polyglutamine domain proteins from tissues outside the central nervous system. Such an effect could be due to the presence of other proteins with higher affinities for GAPDH or the polyglutamine containing proteins, or to differences in pre- or post-translational modifications of the CAG repeat proteins. Alternative splicing has been reported for the SCA1 gene (Banfi et al., *Nature Genetics* 7:513 (1994)) and differential 3' polyadenylation is found within the HD gene. Lin et al., *Hum. Mol. Genet.* 2:1541 (1993). Different size products can also be the result of varying translation start points. Translation of the DRPLA gene is reported to begin at an ATG initiation codon which has an in-frame stop codon 6 bp upstream, but the flanking sequence of the proposed initiation codon is not in good agreement with Kozak's consensus sequence (Onodera, Oyake, Takano, et al., *Am. J. Hum. Genet,* 57:1050(1995)). Nagafuchi et al. have identified a second potential initiation codon approximately 1240 nucleotides 3' to the first ATG and the sequence surrounding this codon is compatible with the Kozak sequence. Nagafuchi et al., *Nature Genet.* 8:177 (1994). The second ATG is still approximately 149 amino acids upstream from the CAG repeat and if used for translation would generate a protein of approximately 850 amino acids. As found by the present inventors, antibody to DRPLA protein recognizes two bands in brain and other tissue; one band migrates at 190 kD and the other at −90 kD. The molecular weight of the −90 kD protein is approximately the expected size for an 850 amino acid protein making it a reasonable candidate for translation from an alternate start site.

Cells treated by the method of the present invention are typically mammalian cells (e.g., human, dog, cat, rat, mouse), and are typically nerve cells, and are particularly nerve cells of the central nervous system. The cells may be treated in vitro or in vivo in an animal host.

Methods of the present invention are useful in analyzing the contribution of GAPDH binding to expanded polyglutamine regions to neurocellular degeneration, both in vitro and in vivo. Methods of the present invention are also useful for inhibiting the degeneration of a nerve cell, which nerve cell has a gene containing an expanded CAG domain which is translated into a polyglutamine region, the method comprising inhibiting the binding of GAPDH to the polyglutamine region. Such methods are useful for prolonging the life of nerve cells that contain such regions when grown in culture (e.g., cultures used for the development or manufacture of vaccines or for the production of other biological products by fermentation).

Suitable subjects for carrying out the present invention are typically male or female human subjects, and include both those which have previously been determined to be at risk of developing a CAG-repeat neurodegenerative disease, and those who have been initially diagnosed as being affected with such a disease. One preferable group of subjects are those who have been determined to carry a gene associated with CAG-repeat neurodegenerative disease, where CAG-repeat domain contains more than 40 CAG triplets.

The term "CAG-domain neurodegenerative disease", as used herein, refers to those inherited neurodegenerative diseases which are due to the presence of a gene having an expanded CAG repeat domain. Such diseases include dentatorubral-pallidoluysian atrophy (DRPLA), Huntington's disease (HD), spinobulbar muscular atrophy (SBMA or Kennedy's disease), Machado-Joseph disease (MJD), spinocerebellar ataxia type 1 (SCA1), and the Haw River syndrome (HRS). The size of the CAG repeat domain necessary to cause neurodegeneration varies among the diseases, but typically pathological changes are not seen when the CAG domain contains fewer than 40 CAG triplets, and in the case of Huntington's disease, fewer than 36 or 37 CAG triplets.

The terms "inhibit" or "inhibiting" (or "combat" or "combatting"), as used herein, are not intended to indicate a reversal of the neurodegenerative or psychiatric disease process, but are instead intended to indicate a slowing of pathological events, such as a delaying of onset of neurologic or psychiatric signs and symptoms or a slowing of the progression of such signs and symptoms. Thus, the method of the present invention may be carried out either therapeutically in a patient where initial signs of CAG-domain neurodegenerative or psychiatric disease are present, or prophylactically in a subject at risk of developing such disease.

As used herein, an 'expanded CAG domain' refers to a region of CAG trinucleotide repeats which contains an increased number of trinucleotide repeats compared to that typically found in the gene.

As used herein, the term "GAPDH binding inhibitor" or "inhibitor" refers to an agent or compound which decreases binding of GAPDH to expanded polyglutamine regions over that which would occur in the absence of the inhibitor. Enzyme inhibitors in general may be classified as competitive inhibitors, noncompetitive inhibitors, or uncompetitive inhibitors. See Segel, *Biochemical Calculations*, John Wiley and Sons, New York, 2d Ed., pp. 246–256 (1976). A competitive inhibitor is a substance that combines with free enzyme in a manner that prevents substrate binding. That is, the inhibitor and the substrate are mutually exclusive, often because of true competition for the same site. A noncompetitive inhibitor has no effect on substrate binding. Substrate and inhibitor bind randomly and independently at different sites. Once a noncompetitive inhibitor binds, however, the enzyme is inhibited. The net effect of a noncompetitive inhibitor is to make it appear as if less total enzyme were present. An uncompetitive inhibitor is a compound that binds to the enzyme-substrate complex yielding an inactive enzyme-substrate-inhibitor complex; an uncompetitive inhibitor does not bind to the free enzyme. A GAPDH substrate may act as a polyglutamine region binding inhibitor, as the presence of a GAPDH substrate decreases the amount of free GAPDH available for binding to polyglutamine regions. Nicotinamide adenine dinucleotide (NAD) is a GAPDH substrate; derivatives of NAD have been designed with enhanced inhibition of parasite GAPDH. Verlinde et al., *J. Medicinal Chem.* 37:3605 (1994). As used herein, GAPDH substrate includes both NAD and NAD derivatives capable of binding to GAPDH. Exogenously administered GAPDH may essentially act as an inhibitor by binding to polyglutamine regions, thus decreasing the amount of endogenous GAPDH which binds to polyglutamine regions. Compounds capable of inhibiting binding of GAPDH to polyglutamine regions may be unrelated, structurally or functionally, to GAPDH provided the compounds act to inhibit binding of GAPDH to the polyglutamine regions.

Fragments of GAPDH which contain the region which specifically binds to the polyglutamine region may also be used as the active agent in the methods herein. Such fragments may be produced by standard techniques. Fragments employed in carrying out the present invention may be peptides derived from GAPDH which have N-terminal, C-terminal, or both N-terminal and C-terminal amino acid residues deleted, but which retain the biological activity of the parent protein as described herein. Such active fragments may be prepared by direct synthesis or by genetic engineering procedures. The terms GAPDH and GAPDH fragments as employed herein include analogs thereof. An "analog" is a chemical compound similar in structure to another and which has a similar physiological action (e.g., another peptide, or a peptidomimetic). Such analogs may initially be prepared by adding, altering or deleting amino acids. For example, from 1 to 5 additional amino acids may be added to the N-terminal, C-terminal, or both the N-terminal and C-terminal of an active fragment. In another example, one (or more) amino acids of a synthetic peptide sequence may be replaced by one (or more) other amino acids, provided the replacement does not affect the activity of that sequence. Analogs may also be small organic compounds (organomimetics) which mimic or have the activity of the parent compound such as GAPDH. Changes in the parent compound to construct the analog can be guided by known similarities between amino acids and other molecules or substituents in physical features such as charge density, hydrophobicity, hydrophilicity, size, and configuration, etc. For example, Thr may be replaced by Ser and vice versa, Asp may be replaced by Glu and vice versa, and Leu may be replaced by Ile and vice versa. Further, the selection of analogs may be made by mass screening techniques known to those skilled in the art (e.g., screening for compounds which bind to the expanded polyglutamine).

Active agents of the present invention may be, administered per se or in the form of a pharmaceutically acceptable salt. Such pharmaceutically acceptable salts include, but are not limited to, those prepared from the following acids: hydrochloric, hydrobromic, sulphuric, nitric, phosphoric, maleic, salicylic, p-toluenesulfonic, tartaric, citric, methanesulphonic, formic, malonic, succinic, naphthalene-2-sulphonic and benzenesulphonic. Also, pharmaceutically acceptable salts can be prepared as alkaline metal or alkaline earth salts, such as sodium, potassium or calcium salts of a carboxylic acid group.

The amount of active agent administered to a subject will vary depending upon the age, weight, and condition of the subject, the particular active agent being delivered, the delivery schedule, and other such factors, as would be apparent to one skilled in the art. When treating subjects, the active agent is delivered in an amount effective to inhibit or combat the neurodegenerative process in neurodegenerative diseases, and in an amount effective to inhibit or combat the psychiatric and neurological pathology of psychiatric disorders.

Pharmaceutical compositions containing the active agents of the present invention may be prepared in either solid or liquid form. To prepare the pharmaceutical compositions of this invention, one or more of the active agents is intimately admixed with a pharmaceutical carrier according to conventional pharmaceutical compounding techniques, which carrier may take a wide variety of forms depending on the form of preparation desired for administration, e.g. oral or parenteral (e.g., intravenous, subcutaneous, intrathecal). In preparing the compositions in oral dosage form, any of the usual pharmaceutical media may be employed. Thus, for liquid oral preparation, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterally injectable compositions, the carrier will usually comprise sterile, pyrogen-free water, or sterile, pyrogen-free physiological saline solution, though other ingredients, for example, for purposes such as aiding solubility or for preservatives, may be included. Parenterally injectable suspensions (e.g., for intravenous or intrathecal injection) may also be prepared, in which case appropriate liquid carriers, suspending agents and the like may be employed.

Compounds as given above may be used for the preparation of a medicament for the treatment of neurodegenerative or psychiatric diseases, as given above.

When necessary, the pharmaceutical composition may be prepared so that the active agent passes through the blood-brain barrier. One way to accomplish transport across the blood-brain barrier is to couple or conjugate the active agent to a secondary molecule (a "carrier"), which is either a peptide or a non-proteinaceous moiety. The carrier is selected such that it is able to penetrate the blood-brain barrier. Examples of suitable carriers are pyridinium, fatty acids, inositol, cholesterol, and glucose derivatives. Alternatively, the carrier can be a compound which enters the brain through a specific transport system in brain endothelial cells, such as transport systems for transferring insulin, or insulin-like growth factors I and II. This combination of active agent and carrier is called a prodrug. Upon entering the central nervous system, the prodrug may remain intact or the chemical linkage between the carrier and active agent may be hydrolyzed, thereby separating the carrier from the active agent. See generally U.S. Pat. No. 5,017,566 to Bodor (applicants specifically intend that the disclosure of this and all other U.S. patent references cited herein be incorporated herein in their entirety).

An alternative method for transporting the active agent across the blood-brain barrier is to encapsulate the carrier in a lipid vesicle such as a microcrystal or liposome. Such lipid vesicles may be single or multi-layered, and encapsulate the active agent either in the center thereof or between the layers thereof. Such preparations are well known. For example, PCT Application WO 91/04014 of Collins et al. describes a liposome delivery system in which the therapeutic agent is encapsulated within the liposome, and the outside layer of the liposome has added to it molecules that normally are transported across the blood-brain barrier. Such liposomes can target endogenous brain transport systems that transport specific ligands across the blood-brain barrier, including but not limited to, transferring insulin, and insulin-like growth factors I and II. Alternatively, antibodies to brain endothelial cell receptors for such ligands can be added to the outer liposome layer. U.S. Pat. No. 4,704,355 to Bernstein describes methods for coupling antibodies to liposomes.

Another method of formulating the active agent to pass through the blood-brain barrier is to prepare a pharmaceutical composition as described above, wherein the active agent is encapsulated in cyclodextrin. Any suitable cyclodextrin which passes through the blood-brain barrier may be employed, including β-cyclodextrin, γ-cyclodextrin, and derivatives thereof. See generally U.S. Pat. No. 5,017,566 to Bodor; U.S. Pat. No. 5,002,935 to Bodor; U.S. Pat. No. 4,983,586 to Bodor.

Another method of passing the active agent through the blood-brain barrier is to prepare and administer a pharmaceutical composition as described above, with the composition further including a glycerol derivative as described in U.S. Pat. No. 5,153,179, the disclosure of which is incorporated herein by reference.

In an alternate embodiment, the present invention is carried out by administering to the subject a vector carry a nucleic acid active agent, which vector is capable of entering nerve cells. Such vectors may be formulated with pharmaceutical carriers and administered in like manner as described above. Suitable vectors are typically viral vectors, including DNA viruses (wherein the nucleic acid active agent is DNA) and RNA viruses, or retroviruses (wherein the nucleic acid active agent is RNA). It is preferred, but not essential, that the vector be a neurotropic vector which preferentially infects nerve cells. Techniques for carrying out gene therapy are known. See, e.g., T. Friedmann, Progress Toward Human Gene Therapy, *Science* 244, 1275 (1989); I. Pastan, U.S. Pat. No. 5,166,059.

Methods for passing genetic material through the blood-brain barrier, particularly vital or retrovital encapsidated material, are described in U.S. Pat. No. 4,866,042 to Neuwelt, the disclosure of which is incorporated herein by reference.

Herpesvirus vectors (e.g., herpesvirus type 1, herpesvirus type 2, cytomegalovirus) are a particular type of vector which may be employed to carry out the present invention. Herpes simplex virus type 1 (HSV-1) vectors are particularly preferred. Such vectors generally comprise at least the encapsidation segments of an HSV-1 DNA genome in an HSV-1 viral capsid. The HSV-1 DNA carries a heterologous DNA insert which either contains the active agent DNA molecule, or contains the DNA molecule which encodes the peptide or protein to be expressed. Where the insert DNA molecule encodes a protein or peptide, the insert is under the control of a promoter operative in nerve cells so that the protein or peptide is expressed in nerve cells. The promoter may be of any suitable origin, including of viral origin (e.g., promoters which control the latency-associated transcripts (LAT-s) of HSV-1; the HSV-1 immediate early 4/5 promoter), and promoters which are normally operable in mammalian nerve cells (e.g., the tau protein promoter). The heterologous insert is typically inserted into any region of the vital genome which is non-essential for culture of the virus to enable the production thereof in cell culture, and if necessary in helper cells. Such herpesvirus vectors are known. See, e.g., A. Geller and X. Breakefield, *Science*, pg 1667 (23 September, 1988); C. Ace et al., *J. Virol.* 63, 2260 (1989); C. Preston et al., PCT Application WO 91/02788.

Also disclosed herein is a method of screening compounds for the ability to inhibit binding of GAPDH to polyglutamine regions, the ability to inhibit neurocellular degeneration due to the presence of proteins containing expanded polyglutamine regions, and/or the ability to inhibit or combat the neurologic symptoms of CAG-domain neurodegenerative diseases. Such a method comprises contacting a test compound to an expanded polyglutamine region (either synthetic or natural) and then detecting whether the test compound binds to the polyglutamine region such that binding of GAPDH is inhibited. Such a method further comprises administering the test compound to affected cells, in vitro or in vivo, and then detecting whether the expected neurodegeneration occurs. The format of the assay and the manner by which the contacting step is carried out is not critical, and a variety of possibilities will be readily apparent to those skilled in the art. Typically, the contacting step is carried out in vitro, in an aqueous solution, and the detecting step is carried out by means of a competitive binding assay in which a known compound which binds to the polyglutamine region, such as GAPDH, is included in the solution, and the ability of the test compound to inhibit the binding of the GAPDH is determined. For such assays, the known compound is labelled with a suitable detectible group, such as tritium. Other assays, such as gel mobility shift assays, may also be employed. The presence of binding to the polyglutamine region indicates the test compound is or may be useful for achieving one or more of the effects noted above. Compounds detected in this manner are useful for the in vitro and in vivo study of the pathogenesis and treatment of CAG repeat neurodegenerative diseases.

The present invention is explained in greater detail in the following Examples, where g means gravity, gm means gram, mg means milligram, ml means milliliter, μl means microliter, mM means milliMolar, v/v means volume/volume, kDa means kiloDalton, ° C. means degrees Centigrade, DRPLA means dentatorubralpallidoluysian, and GAPDH means glyceraldehyde-3-phosphate dehydrogenase. These Examples are for illustrative purposes and are not to be taken as limiting of the invention.

EXAMPLE 1

GAPDH in Brain Homogenate Binds to a 60-Glutamine Peptide

Normal cortical brain homogenate was incubated with an immobilized synthetic 20-glutamine peptide (representing the product of a native CAG domain size), or with a 60-glutamine peptide (representing an expanded CAG domain). Twenty and 60-glutamine peptides were synthesized on polystyrene beads as has been described (W. Strittmatter et al., *Proc. Natn. Acad. Sci. USA* 90:8098–8102 (1993)). The peptides were not cleaved from the polystyrene beads but were left attached. Frozen cortical brain samples (0.5 gm) from neurologically normal controls were obtained and parietal cortex tissue was suspended in ten volumes of ice-cold 25 mM MOPS pH 7.3, PBS (MOPS/PBS), homogenized using a Kontes glass homogenizer and centrifuged at 43,000×g for 30 minutes at 4° C. The supernatant was removed and incubated with 25 mg of the immobilized polyglutamine peptide resin in 500 μl MOPS/PBS overnight at 4° C. The polyglutamine resins were washed with 1 ml MOPS/PBS and protein was eluted with 100 mM glycine pH 3.0. Eluted protein was mixed with an equal volume of Laemmli sample buffer (2% SDS/ 5% (v/v) 2-mercaptoethanol/10% (v/v) glycerol/62.5 mM Tris-HCl pH 6.8) and electrophoresed on a 12% polyacrylamide gel with 2% SDS. Proteins were visualized by silver stain (Bio-Rad). Protein band (a) (as seen in FIG. 1) was microsequenced by automated Edman degradation with an Applied Biosystems 477A sequencer with on-line phenylthiohydantoin analysis using Applied Biosystems 120A HPLC.

Of proteins in brain homogenate (FIG. 1, Lane 3), only a small number bound to the immobilized 20-glutamine peptide (FIG. 1, Lane 1) or the 60-glutamine peptide (FIG. 1, Lane 2). The protein labeled (a) in FIG. 1 was retained only by the 60-glutamine peptide, and was microsequenced through its amino terminus as Val-Lys-Val-Gly-Val-Asn-Gly-Phe-Gly-Arg-Ile-Gly-Arg-Leu-Val-Thr-Arg-Ala (VKVGVNGFGR IGRLVTRA) (SEQ ID NO:1). A computerized data base search revealed a sequence identity with the amino terminus of glyceraldehyde-3-phosphate dehydrogenase (GAPDH; Enzyme Commission (EC) 1.2.1.12). GAPDH has a relative molecular weight of 36 kDa, identical to that of protein (a). In addition, anti-GAPDH antibodies confirmed the identity of protein (a) on Western blots (not shown).

These data indicate that GAPDH selectively binds to expanded glutamine peptides (60 mer) but not to 20-glutamine peptides.

EXAMPLE 2

Brain Proteins Containing Polyglutamine-Domains Bind GAPDH

To determine what brain proteins bind to GAPDH, rabbit muscle GAPDH (Calbiochem) was coupled to AminoLink gel according to manufacturers instructions (Pierce) or to agarose beads following cyanogen bromide linkage (Sigma). 300 µl of amino-coupled GAPDH resin was washed 5 times with 25 mM MOPS pH 7.3, PBS (MOPS/PBS). Brain supernatant fractions prepared as described in Example 1 were concentrated in Centricon 100 filtration units (100 kDa exclusion, Amicon) by centrifugation at 1,000×g for 60 minutes at 4° C. An aliquot of concentrated supernatant containing 250 mg protein was incubated overnight with immobilized GAPDH at 4° C. After incubation, the agarose was centrifuged and the supernatant collected. The agarose was then washed 4 times in 400 µl MOPS/PBS, and bound protein was eluted with two 300 µl aliquots of 2% formic acid. Unbound material and eluted proteins were concentrated using Centricon concentrators (Amicon) with 30 kDa exclusion. The eluted samples were dried using a Speed-Vac to remove the remaining formic acid. Laemmli sample buffer with 2-mercaptoethanol was added to the samples, and the proteins were electrophoresed on a denaturing 7.5% polyacrylamide reducing gel at 200 V.

Figure 2A:
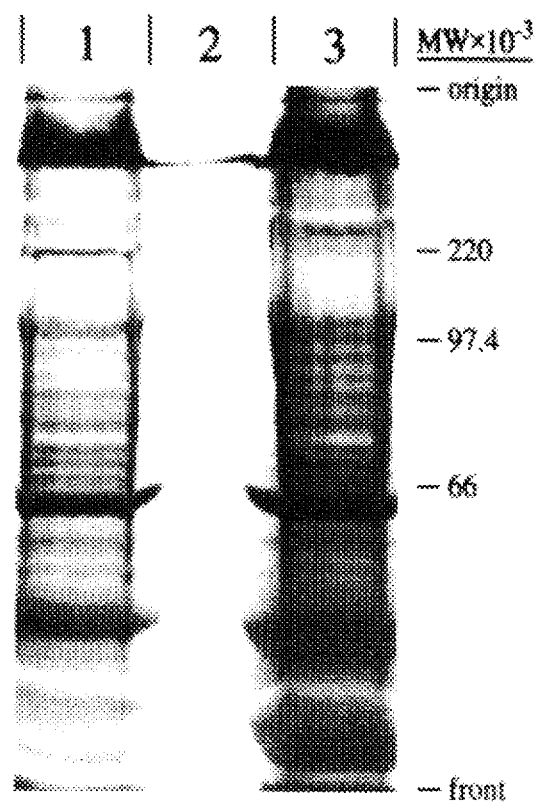
FIG. 2A shows a silver stained SDS polyacrylamide gel showing binding of DRPLA protein to immobilized GAPDH. Lane 1 is the supernatant of brain homogenate; Lane 2 is protein eluted from immobilized GAPDH by formic acid; Lane 3 is protein not bound by immobilized GAPDH.
Figure 2B:
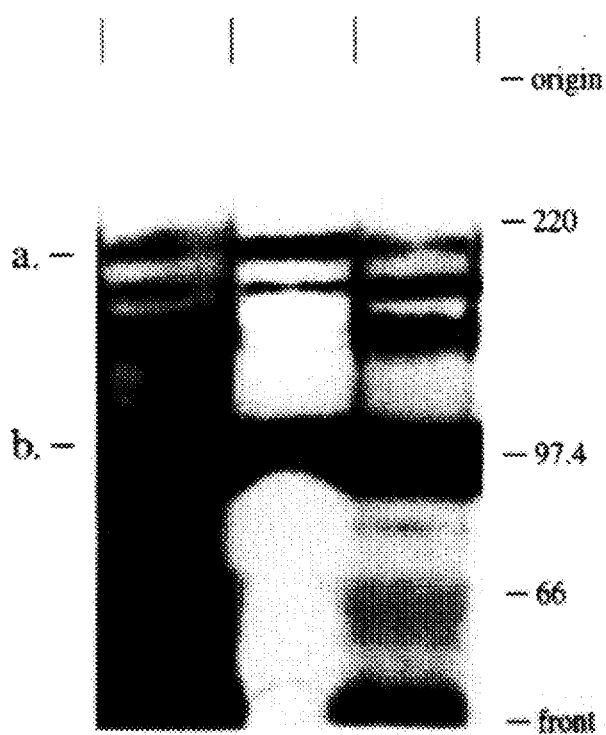
FIG. 2B is a Western blot probed with anti-DRPLA antibody and showing DRPLA protein which bound to GAPDH. Lane 1 is the supernatant of brain homogenate; Lane 2 is protein eluted from immobilized GAPDH by formic acid; Lane 3 is protein not bound by immobilized GAPDH. The designation (a) indicates 190 Kda DRPLA protein and (b) indicates 100 Kda DRPLA protein.

The gels were either stained for protein using Bio-Rad (Hercules, Calif., USA) silver stain (FIG. 2A) or transferred to Immobilon P membranes for incubation with an anti-DRPLA antibody (FIG. 2B).

In FIG. 2A, Lane 1 contains supernatant of brain homogenate; Lane 2 contains protein eluted from immobilized GAPDH by formic acid; and Lane 3 contains protein not bound by immobilized GAPDH. Only a few proteins bound to the immobilized GAPDH (FIG. 2A, Lane 2).

The anti-DRPLA antibody was prepared against amino acids 1168–1184 of the DRPLA protein (S. Nagafuchi et al., Nature Genet. 8:177–182 (1994)) injected into rabbits. Peptide synthesis and immunizations for the DRPLA antibody were performed by Quality Controlled Biochemicals (Hopkinton, Mass.). Peptide antigen was conjugated to keyhole limpet hemocyanin as carrier. Immobilon P membranes were blocked in Blotto (5% nonfat dry milk, 0.05% TWEEN®–20 in TBS pH 7.6) for one hour at room temperature. The membrane was incubated with the DRPLA antibody (1:500) in Blotto overnight at 4° C. with shaking. Membranes were washed in Blotto, then incubated with secondary antibody. The secondary antibody, goat-antirabbit IgG conjugated with horseradish peroxidase (1:5000; Boehringer Mannheim) was incubated at 1 hour at room temperature. Signal was detected using the Enhanced Chemiluminescence (ECL) system (Amersham) with exposure to Hyperfilm (Amersham).

FIG. 2B depicts the Western blots probed with anti-DRPLA antibody, where Lane 1 contains supernatant of brain homogenate; Lane 2 contains protein eluted from immobilized GAPDH by formic acid; and Lane 3 contains protein not bound by immobilized GAPDH. The designation (a.) indicates 190 kDa DRPLA protein and (b.) indicates a 100 kDa DRPLA protein. In control (neurologically normal) brain, the anti-DRPLA antibody recognized proteins of 190 kDa and 100 kDa (FIG. 2B, labelled (a.) and (b.)), identical to native DRPLA protein described by Yazawa et al. (I. Yazawa et al., Nature Genet. 10:99–103 (1995)). In the material eluted from immobilized GAPDH by formic acid, this anti-DRPLA antibody detected two strongly reactive proteins of 190 and 100 kDa (FIG. 2B, Lane 2).

In the above studies, binding of DRPLA proteins to GAPDH was observed in brain homogenates from each of three neurologically normal control brains examined.

EXAMPLE 3

Binding of Huntingtin Protein and Fragments to GAPDH

Figure 3:
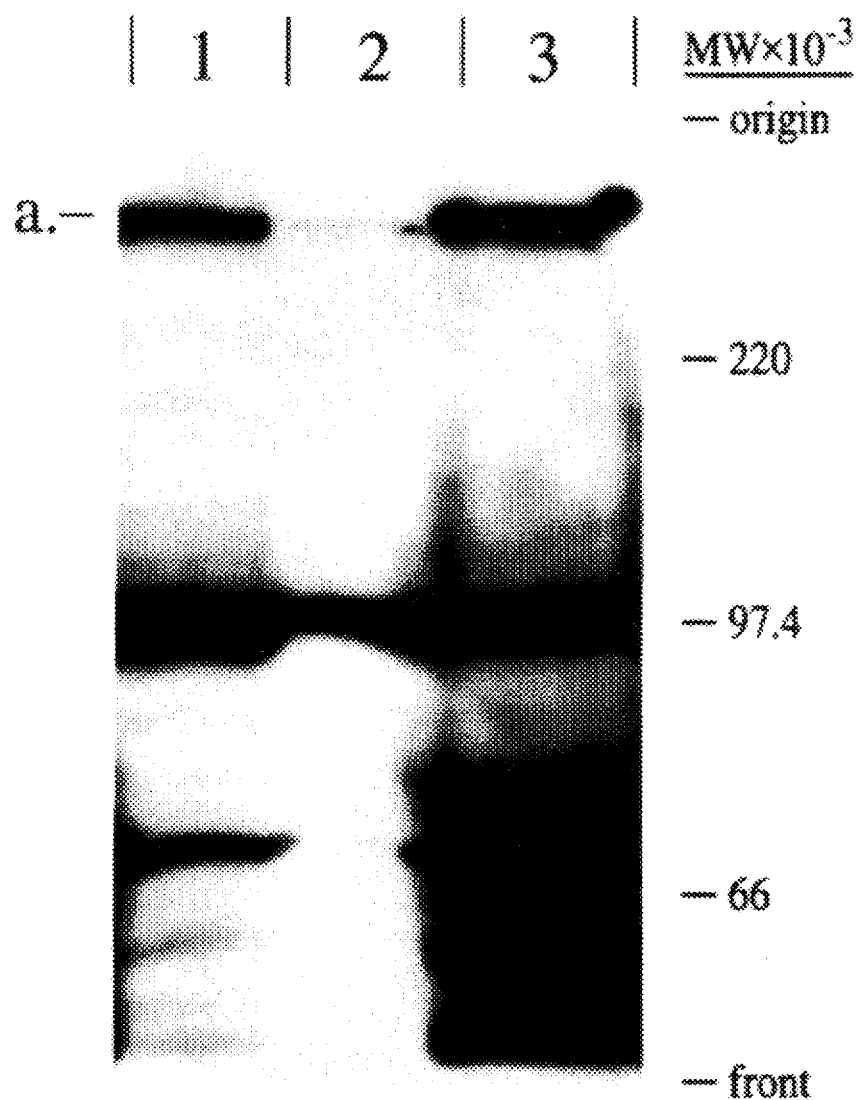
FIG. 3 is a Western blot probed with anti-huntingtin antibody and showing binding of huntingtin protein and huntingtin fragments to immobilized GAPDH. Lane 1 contains proteins from homogenized brain supernatant; Lane 2 contains brain proteins which bound to immobilized GAPDH; and Lane 3 contains proteins which did not bind to immobilized GAPDH. The designation (a) indicates full length huntingtin.

FIG. 3 shows the binding of huntingtin and huntingtin fragments to immobilized GAPDH. Brain homogenate was incubated with immobilized GAPDH (as described above in Example 2). The anti-huntingtin antibody used for detection was prepared against amino acids 11–19 of the huntingtin protein (Y. Jou and R. Myers, Human Molec. Genetics 4:465–469 (1995)). Detection of huntingtin binding to GAPDH was as described in Example 2 for DRPLA protein.

Full-length neurologically normal huntingtin (347 kDa) was detected in brain homogenate by the anti-huntingtin antibody (FIG. 3, Lane 1, labeled (a.)), but full-length huntingtin demonstrated only minimal binding to cyanogen bromide immobilized GAPDH (FIG. 3, Lane 2). The antibody, which recognizes the amino-terminus of huntingtin which contains the polyglutamine domain, also identified several huntingtin fragments which bound GAPDH (FIG. 3, Lanes 2 and 3).

Full-length neurologically normal huntingtin bound to immobilized GAPDH and huntingtin fragments bound, under the present conditions, to a greater degree. Binding of full-length huntingtin may be sterically hindered by its own carboxy-terminus or by the immobilization of GAPDH to agarose. The immunoreactive huntingtin fragments observed in the present Example were also observed by Jou and Myers (Y. Jou and R. Myers, Human Molec. Genetics 4:465–469 (1995)). It is not yet known whether these fragments are produced by proteolysis of full-length huntingtin or by alternative splicing.

The results of Examples 1, 2 and 3 indicate that GAPDH binds preferentially to "expanded" glutamine peptide (60-mer), and that GAPDH forms complexes with polyglutamine-containing peptides such as huntingtin and DRPLA. These results suggest that the interaction of GAPDH and polyglutamine-containing peptides may be biologically relevant in neurologic diseases associated with CAG trinucleotide repeat expansion, by modifying some or all of GAPDH activities as a function of polyglutamine repeat length.

EXAMPLE 4

Inhibition of GAPDH Activity by 60-mer Polyglutamine Regions

GAPDH is an essential enzyme in glycolysis and gluconeogenesis, converting glyceraldehyde-3-phosphate to 1,3-diphosphoglycerate using $NAD^+$ as a cofactor. The present Example measured the effects of polyglutamine regions on this reaction.

Ammonium sulfate precipitated rabbit muscle GAPDH (Boehringer-Mannheim) was dissolved in 25 mM MOPS/PBS buffer pH7.3 (MOPS/PBS) and incubated with polystyrene beads containing 60-mer glutamine peptide for 30 minutes on ice. Rabbit muscle and rabbit brain GAPDH are identical in sequence (Kochman et al., Biochemistry 7:1671 (1968)) and are approximately 90% identical to human enzyme (Tso et al., Nucleic Acids Res 13:2485 (1985)). GAPDH activity was measured using a 3ml reaction volume containing MOPS/PBS, 500 µM $NAD^+$, 50 µM glyceraldehyde-3-phosphate and 5 mM $NaASO_4$. $NaASO_4$ is used to increase the duration of linearity of the assay. It irreversibly inhibits the conversion of 1,3-diphosphoglycerate to glyceraldehyde-3-phosphate by forming 1-arseno, 3-phosphoglycerate which can not be used as a substrate by GAPDH. GAPDH activity was measured by following the increase in absorbance at 340 nm as $NAD^+$ is converted to NADH, using a Gilson recording spectrophotometer with a kinetic analysis package. The rate of the reaction is determined by measuring the slope of the increase in absorbance from 0 to 0.5 minutes, and the maximum product synthesized from the absorbance at equilibrium (Scheek et al., In: Wood WA (Ed.), Methods in Enzymology, Volume 89, Academic Press, New York, 305–309 (1982)).

Figure 4:
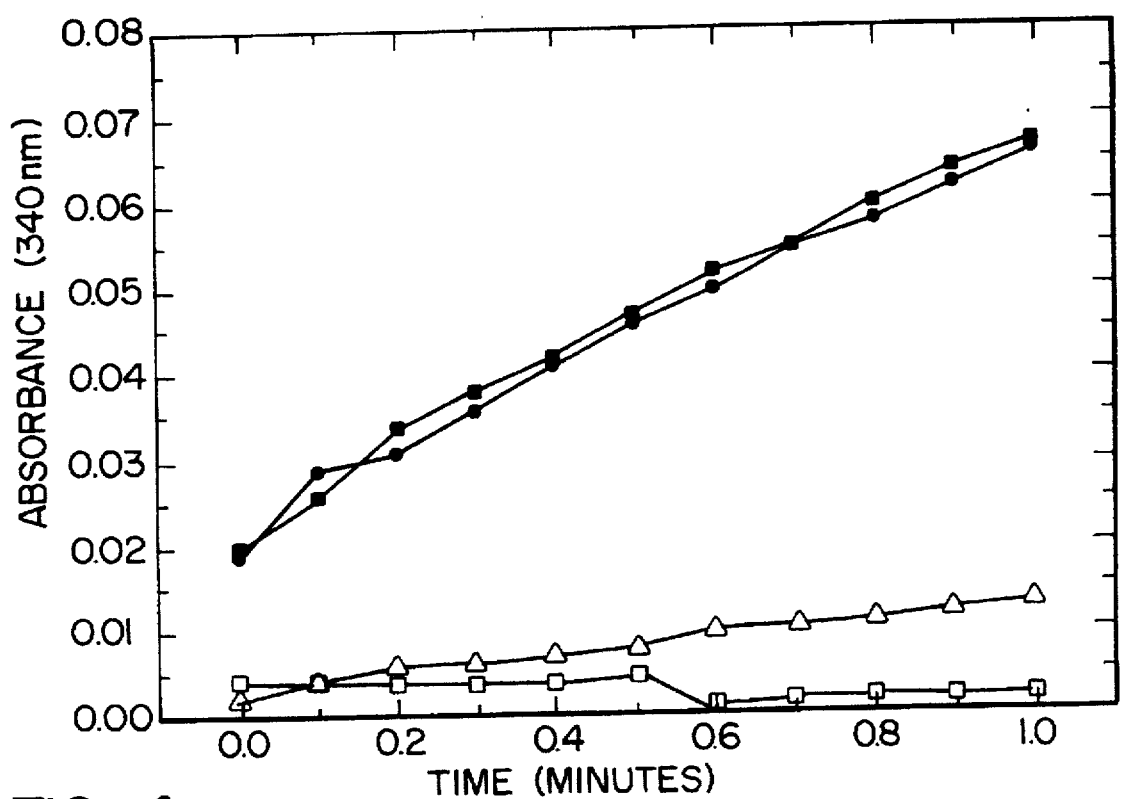
FIG. 4 graphs GAPDH glycolytic activity by spectrophotometric monitoring of the production of NADH. Closed squares indicate GAPDH plus polystyrene beads containing 1 glutamine (control; ratio 1:150 GAPDH:glutamine); closed circles indicate GAPDH plus polystyrene beads containing 60-mer glutamine in a ratio of 1:25 (GAPDH:polyglutamine); open triangles indicate GAPDH plus polystyrene beads containing 60-mer glutamine in a ratio of 1:50 (GAPDH:polyglutamine); open squares indicate GAPDH plus polystyrene beads containing 60-mer glutamine in a ratio of 1:100 (GAPDH:polyglutamine).

60-mer polyglutamine was immobilzed on polystyrene beads and incubated with GAPDH for 30 minutes prior to the addition of substrate and cofactor. After addition of substrate and cofactor GAPDH activity was assessed by spectrophotometrically monitoring the production of NADH, by measuring any increase in absorbance at 340 nm. At ratios of 1:25 (mol GAPDH:mol polyglutamine peptide) no inhibition of GAPDH activity was detected (FIG. 4). At a ratio of 1:50 the rate of reaction was inhibited by 80%. At a ratio of greater than 1:100 there was complete inhibition of NADH production. Polystyrene beads containing 1 glutamine (controls) had no effect on the rate of the reaction.

EXAMPLE 5

Inhibition of GAPDH Activity by Polyglutamine Regions of Varying Lengths

The effects of polyglutamine regions of varying size on GAPDH conversion of glyceraldehyde-3-phosphate to 1,3-diphosphoglycerate are further studied using rabbit GAPDH as above with immobilized synthetic polyglutamine peptides containing 20, 40 and 60 glutamines. Polystyrene beads containing a single glutamine are used as a control. The ability of the polyglutamine peptides to inhibit GAPDH's activity is compared at various ratios of GAPDH:polyglutamine peptide (molar:molar comparison calculated on the molecular weight of GAPDH and polyglutamine and the theoretical yield of peptide synthesis on polystyrene beads (0.55 mmol/gm beads)). The polyglutamine concentration is overestimated by this method because peptide synthesis is not 100% efficient but the experimental yield should be similar for the varying lengths of homopolymer.

The change in reaction rate is a primary measure of the effect of polyglutamine binding on GAPDH activity. The percentage change in the reaction rate is calculated by dividing the rate in the presence of polyglutamine peptide containing polystyrene beads by the rate in the presence of beads containing one glutamine (×100). The ratio of GAPDH:polyglutamine that causes 50% inhibition is determined for each length peptide (see Example 4).

The effect of varied length polyglutamine regions on the rate of complex formation with GAPDH is also studied. To determine if rate of complex formation is a function of polyglutamine length, GAPDH is incubated with polyglutamine peptides for varying periods of time (0–2 hours) and then assayed for changes in the reaction rate. The effects of the varied length peptides are compared at each time point. Changes in the rate of complex formation between apolipoprotein E isoforms and β-amyloid peptide has been demonstrated using a similar protocol. Strittmatter et al, Proc. Natl. Acad. Sci. 90:8098 (1993).

Polyglutamine affinity for interaction with GAPDH is also studied as a function of repeat size. The affinity of the complex is assayed indirectly by assaying GAPDH activity following incubation with polyglutamine peptides of different lengths at different ionic strengths and pH. Preliminary results of experiments conducted by the present inventors have indicated that complex formation was dependent on pH. At pH 9.0 glutamine 60-mer peptides did not inhibit GAPDH glycolytic activity even at molar ratios of 1:250 (GAPDH:polyglutamine).

Demonstration of a glutamine length dependent change in GAPDH activity, with increasing effects seen with expanded polyglutamine regions, indicates that GAPDH-polyglutamine protein interactions are involved in CAG repeat disease pathogenesis, and would be consistent with the observed correlation between repeat length and disease severity.

EXAMPLE 6

GAPDH Activity in Tissue Samples

GAPDH glycolytic and glycosylase activity are compared using crude homogenates from tissues and cell lines from normal individuals, individuals with neurodegenerative diseases other than CAG repeat diseases (e.g., Alzheimer's Disease), and those with CAG repeat diseases. Homogenates are dialyzed to remove endogenous substrate and cofactors. Tissue samples are presently available from patients with Huntington disease, and cell lines are available from patients with DRPLA and spinocerebellar ataxia type 1. GAPDH specific activity is determined for each sample to determine differences associated with disease states.

EXAMPLE 7

DRPLA Protein Expression

Complete DRPLA cDNA clones containing normal and pathologic numbers of CAG repeats were obtained from Dr. Tsuji, Niigata University, Japan. Cloning and expression techniques known in the art were used to produce fragments of DRPLA protein. Portions of cDNA containing the CAG repeats may be isolated by restriction digestion or amplified by PCR to produce subclones containing fragments of interest, including the region surrounding and containing the polyglutamine region. Inserts are subcloned into the expression vector pGEX-4T-3 (Pharmacia) and transformed into E. coli strain BL21, as pGEX-4T-3 produces a GST fusion protein with the inserted DRPLA sequences allowing easy purification of the hybrid protein. A similar approach has been used to generate full-length functional human androgen receptor (Roehrborn et al., Mol. Cell. Endocrinol. 84:1 (1992)) and a 70 kDa fragment of the DRPLA protein containing the polyglutamine repeat (Yazawa et al., Nature Genet. 10:99 (1995)). Protein expression may be induced by addition of IPTG.

Sma-1 inserts from DRPLA cDNA (nucleotide 238-2090 of Genbank accession number D38529; SEQ ID NO:2; see Onodera et al., Am. J. Hum. Genet, 57:1050(1995)) were subcloned with normal sized and expanded CAG repeats into pGEX-4T-3 to produce GST fusion proteins of approximately the expected size. The fusion proteins containing the normal and expanded CAG repeat showed the expected slight differences in molecular weight due to the presence of variable numbers of glutamine.

Other approaches to increase full-length expression of DRPLA include modifying incubation or isolation conditions (e.g., time, temperature, presence of protease inhibitors, or supplementation of growth media), host strains, or converting to other prokaryotic (such as a histidine tagged vector) or eukaryotic baculovirus) expression vectors.

EXAMPLE 8

Digestion of GAPDH to Produce Fragments

Figure 5:
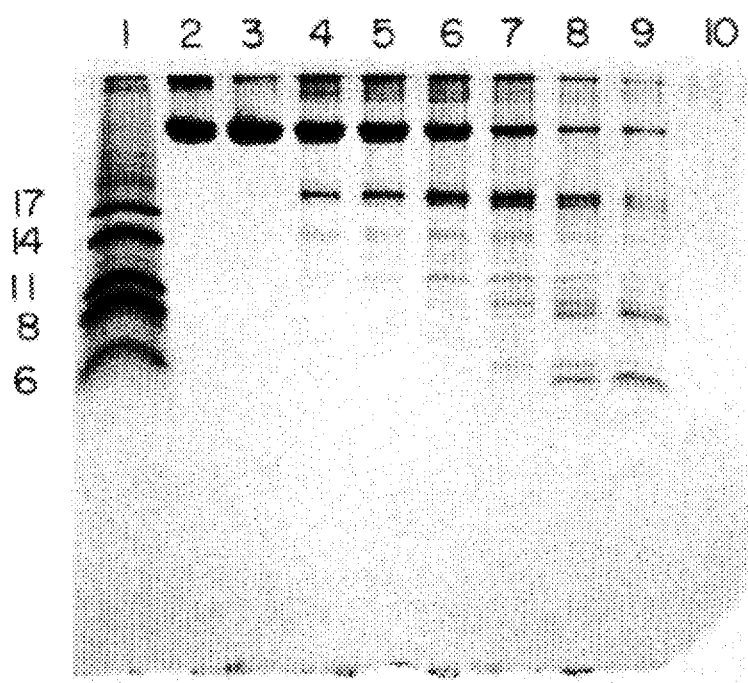
FIG. 5 is a tricine gel electrophoresis of trypsin digestion products from GAPDH. Lane 1 contains molecular weight standards ($\times 10^{-3}$); Lane 2 contains GAPDH nonreduced; Lane 3 contains GAPDH reduced with beta-mercaptoethanol; Lane 4 contains GAPDH:trypsin 1:20,000 w/w; Lane 5 contains GAPDE:trypsin 1:10,000 w/w; Lane 6 contains GAPDH:trypsin 1:2,000 w/w; Lane 7 contains GAPDH:trypsin 1:1,000 w/w; Lane 8 contains GAPDE:trypsin 1:200 w/w; Lane 9 contains GAPDH:trypsin 1:100 w/w; Lane 10 contains trypsin alone.

Trypsin was incubated with rabbit muscle GAPDH for one hour at 37° under reducing conditions at varying ratios (GAPDH:trypsin of 1:20,000 w/w; 1:10,000 w/w; 1:2,000 w/w; 1:1,000 w/w; 1:200 w/w; or 1:100 w/w). The products were run on a tricine polyacrylamide gel and the gel was stained with coomassie blue. Results are shown in FIG. 5. A ratio of 1:200 resulted in complete digestion of GAPDH and will be used for isolation of GAPDH fragments using reversed phase HPLC.

EXAMPLE 9

Binding of GAPDH Fragments to Polyglutamine Regions

Binding of fragments of GAPDH to polyglutamine peptide is used to confirm and refine the location of the likely binding domain identified by enzymatic analysis as described in Example 10. Tryptic digests of GAPDH are incubated with polyglutamine peptide immobilized on polystyrene beads to determine which fragments of GAPDH bind to polyglutamine peptide of varying lengths 20, 40, 60 glutamines). Comparisons of the GAPDH fragments that bind identify fragments that preferentially bind one length polyglutamine. Beads containing a single glutamine are used as a control. GAPDH fragments which bind to polyglutamine peptide are eluted using formic acid and electrophoresed on a polyacrylamide gel, transferred to immobilon membranes using the Western technique, and the membrane stained with coomassie blue. Coomassie blue bands of interest are excised and microsequenced. Isolated fragments of GAPDH that bind to polyglutamine are compared with the findings from the kinetic studies using G3P and $NAD^+$, as well as to the results from incubation of the entire tryptic digest.

Use of a mixture of tryptic fragments of GAPDH allows comparison of multiple fragments for the ability to bind to 20-mer and 60-mer glutamine peptides. Tryptic digest fragments of GAPDH purified by reversed phase high performance liquid chromatography (HPLC) are used to determine which fragments bind. In reversed phase HPLC the peptides are adsorbed onto a $C_{18}$ column under aqueous conditions that favor hydrophobic interactions between the peptide and the column. The peptides are eluted from the column using a linear gradient of 0–20% acetonitrile, 0.1% trifluoroacetic acid (TFA) for 90 minutes, followed by 20–60% acetonitrile, 0.1% TFA for 30 minutes with monitoring absorbance of the eluted material at 214 nm.

Fragments of GAPDH found to bind to polyglutamine are then used to examine their effect on polyglutamine and DRPLA protein inhibition of GAPDH activities (e.g., glycolysis, uracil DNA glycosylase and GAPDH stimulated tubulin polymerization).

Several different cleavage methods may be used to produce GAPDH fragments of different sizes. Banas et al., *Comp. Biochem. Physiol. (B)* 87:391 (1987). Data generated using fragments produced by different methods may be compared for consistency. Expression cloning is an alternative method for specific fragment generation; GAPDH clones are available commercially (Clontech).

EXAMPLE 10

Enzymatic Analysis of GAPDH and Polyglutamine Peptide Binding Site

A GAPDH glycolysis assay is used to identify the region of GAPDH which interacts with polyglutamine peptide. The 3-dimensional crystalline structure of GAPDH contains separate binding domains for glyceraldehyde-3-phosphate (G3P) and $NAD^+$. Harris et al., Glyceraldehyde-3-phosphate dehydrogenase, In Boyer (Ed.), *The Enzymes*, Academic Press, New York, 1–49 (1976). Polyglutamine may bind to one of these domains or to a separate site in the GAPDH molecule. Concentrations of G3P or $NAD^+$ are experimentally increased to study whether a concomitant reduction in polyglutamine-induced inhibition of GAPDH occurs.

GAPDH is incubated with G3P or $NAD^+$ prior to addition of polyglutamine. Polyglutamine is added and allowed to incubate with the enzyme. The reaction is started by addition of either cofactor or substrate and the reaction is followed spectrophotometrically as described in Example 4. A reduction in the polyglutamine inhibition of GAPDH function by G3P or $NAD^+$ implicates that respective domain as involved in polyglutamine-protein interactions.

EXAMPLE 11

Tissue Specific Attributes of DRPLA

Pathology due to the CAG trinucleotide repeat proteins is almost exclusively located in the central nervous system, although polyglutamine containing proteins are widely expressed in the tissues of the body. Tissue-specific attributes of the proteins may explain this pathology.

Figure 6:
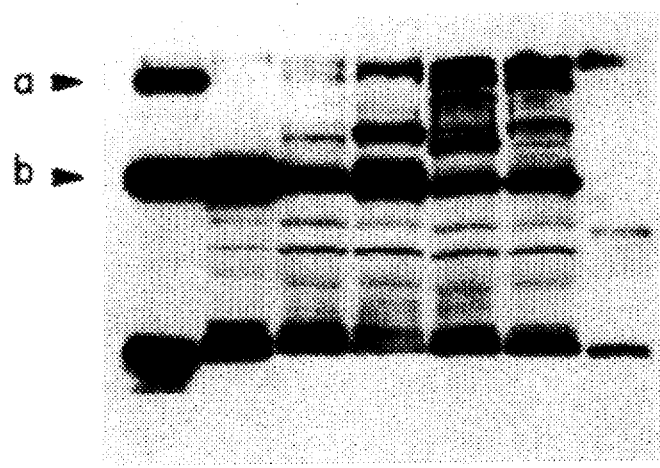
FIG. 6 is a Western blot probed with anti-DRPLA antibody and demonstrating the electrophoretic mobility of DRPLA protein from various human tissues, where Lane 1 is brain tissue; Lane 2 is heart tissue; Lane 3 is kidney tissue; Lane 4 is liver tissue; Lane 5 is lung tissue; Lane 6 is spleen tissue; and Lane 7 is lymphoblast culture.

The electrophoretic mobility of DRPLA protein from different tissues was compared. Tissue homogenates were prepared from brain, heart, kidney, liver, lung, and spleen, and from lymphoblast cultures, from two different neurologically normal human subjects. Both subjects were autopsied less than 1 hour after death to obtain frozen cortical brain samples (0.5 g). Parietal cortex tissue was suspended in ten volumes of ice-cold 25 mM MOPS pH 7.3, PBS (MOPS/PBS), homogenized in a hand-held glass Kontes homogenizer, and centrifuged at 43,000×g for 30 minutes at 4° C. Equal volumes of the supernate were diluted in Laemmli sample buffer containing 2-mercaptoethanol and loaded on a 7.5% SDS polyacrylamide gel. After electrophoresis, the gels were transferred to immobilon membranes and probed with antibody to the carboxyl terminus of DRPLA protein. Results are shown in FIG. 6, where Lane 1 is brain tissue; Lane 2 is heart tissue; Lane 3 is kidney tissue; Lane 4 is liver tissue; Lane 5 is lung tissue; Lane 6 is spleen tissue; and Lane 7 is lymphoblast culture.

Brain DRPLA appeared primarily as a doublet of 190 kD (a in FIG. 6) and 90 kD (b in FIG. 6), but a small amount of higher molecular weight material was also seen. This material migrated above the upper (a) band. "Full-length" DRPLA protein in tissue other than brain consisted mostly of protein that migrated above the major 190 kD brain protein. In kidney (Lane 3) and liver (Lane 4) the expression of the upper band and the 190 kD band appeared equal. Heart (Lane 2) and lymphoblast culture (Lane 7) contained no DRPLA protein migrating at 190 kD, the size of the major species of DRPLA from brain tissue. All of the samples except that from lymphoblast culture contained the 90 kD species. There are also a series of immunoreactive proteins with molecular weights <190 kD in tissues other than brain. It is not known if these are due to proteolysis of larger proteins, pre- or post-translational modification or complex formation of lower molecular weight DRPLA with other proteins. DRPLA protein tissue expression was identical in the two individuals studied. Similar results were obtained using mouse tissues (data not shown).

The appearance of high molecular weight immunoreactive DRPLA protein (>200 kD) was greatly increased in most tissue by running samples under nonreducing conditions (i.e., without beta-mercaptoethanol), but there was only a modest change in results using brain tissue (data not shown). Similar high molecular weight complexes have been reported using sucrose gradient centrifugation with huntington and DRPLA protein (Sharp et al., *Soc. for Neurosci.* 21:685.5 (Abstract) (1995)).

The above data indicates that DRPLA protein from various tissue migrates differently on reducing SDS-polyacrylamide gels. This result may be due to DRPLA protein complex formation with other proteins or to differences in synthesis or processing. These differences are accentuated in nonreducing gels where DRPLA protein from nonbrain tissue migrated as a series of very high molecular weight complexes while in brain these complexes are markedly reduced or absent. It is unlikely that these results are due to proteolysis as identical findings were seen in tissue from a second individual and similar results were obtained with mouse tissues (data not shown).

EXAMPLE 12

Tissue Specific Binding of DRPLA

Tissue homogenates from brain, heart, kidney, liver, lung and spleen are prepared as described in Example 11, and are assayed for binding to GAPDH immobilized on agarose beads (as in Example 2). Homogenates are incubated with immobilized GAPDH, washed and eluted with formic acid. Bound proteins are then electrophoresed on an SDS polyacrylamide gel and transferred to immobilon membranes. The presence or absence of DRPLA protein is determined by probing using anti-DRPLA antibody. Tissue-specific differences in DRPLA protein-GAPDH interaction are elucidated, with maximal binding postulated to occur in brain tissue.

EXAMPLE 13

Alternative Transcription and Translation of DRPLA

Alternative splicing of DRPLA transcripts is evaluated using reverse transcription-polymerase chain reaction (RT-PCR) to generate copies of all species of mRNA present in an original RNA sample. If alternative splicing of DRPLA transcripts occurs, varying size bands following PCR will reflect the different length mRNAs in the original sample. Total RNA is isolated from varied tissues (e.g., brain, heart, lung, liver) and mixed with random hexamer deoxynucleotide primers at 68° for 5 minutes and then chilled quickly to allow hybridization. cDNA is synthesized from the RNA template by addition of Moloney murine leukemia virus reverse transcriptase and all four dNTPs. Aliquots of the "cDNA" are then subjected to PCR using primers specific for the DRPLA gene. Oligonucleotide PCR primers are chosen so that all 9 exons of the DRPLA gene are examined. Primers are chosen to give PCR products of 250–1000 base pairs. Alternative splicing is indicated by multiple size PCR products. The pattern of PCR products synthesized from the different tissues are compared to determine tissue-specific alternative splicing.

Potential alternate translation start sites are identified by microsequencing the amino-terminus of the 90 kDa protein and comparing it to the published sequence. The protein is isolated by incubating brain homogenate with immobilized GAPDH and eluting bound proteins with formic acid. Eluted proteins are transferred to Western blots, coomassie blue stained and the band of appropriate size is excised and sequenced. See Strittmatter et al. *Proc. Natl. Acad. Sci USA* 90:8098 (1993).

EXAMPLE 14

GAPDH Uracil DNA Glycosylase (UDG) Activity

GAPDH uracil DNA glycosylase (UDG) activity is measured using the assay described by Sirover (Col and Sirover, *Cancer Res.* 49:3029 (1989); Meyer-Siegler et al., *Proc. Natl. Acad. Sci. USA.* 88:8460 (1991)). The enzyme UDG removes uracil by base excision. UDG is assayed by measuring release of ethanol or acid-soluble radioactivity from [$^3$H]uracil-labelled DNA templates. Radioactively labelled templates are prepared by copying either activated calf thymus DNA or polydeoxyadenylate-oligodeoxythymidylate with *E. coli* DNA polymerase I, using [$^3$H]dUTP and the appropriate dexoynucleoside triphosphates as precursors. GAPDH uracil DNA glycosylase (UDG) activity is measured in the presence of varying length polyglutamine peptides (e.g., 10, 20 and 60 glutamine repeats) and in the presence of recombinately synthesized DRPLA protein.

EXAMPLE 15

GAPDH Tubulin Polymerization Activity

Tubulin polymerization is determined using the procedure described by Goedert and Jakes (Goedert and Jakes, *EMBO J.* 9:4225 (1990)). Tubulin polymerization is followed spectrophotometrically by measuring the change in turbidity at 350 nm. The rate of polymerization is calculated by measuring the initial slope of the curve. GAPDH tubulin polymerization activity is measured in the presence of varying length polyglutamine peptides (e.g., 10, 20 and 60 glutamine repeats) and in the presence of recombinately synthesized DRPLA protein.

The foregoing examples are illustrative of the present invention, and are not to be construed as limiting thereof. The invention is defined by the following claims, with equivalents of the claims to be included therein.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 18 amino acids
        ( B ) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:1:

| Val | Lys | Val | Gly | Val | Asn | Gly | Phe | Gly | Arg | Ile | Gly | Arg | Leu | Val | Thr |
|---|---|---|---|---|---|---|---|---|---|---|---|---|---|---|---|
| 1 | | | | 5 | | | | | 10 | | | | | 15 | |

Arg Ala ( 2 ) INFORMATION FOR SEQ ID NO:2:

( i ) SEQUENCE CHARACTERISTICS:
( A ) LENGTH: 1853 base pairs
( B ) TYPE: nucleic acid
( C ) STRANDEDNESS: single
( D ) TOPOLOGY: linear ( i i ) MOLECULE TYPE: peptide ( x i ) SEQUENCE DESCRIPTION: SEQ ID NO:2:

| | | | | | | |
|---|---|---|---|---|---|---|
| GAAAGTGAGG | AGACCAATGC | ACCAAAAAAG | ACCAAAACTG | AGCAGGAACT | CCCTCGGCCA | 60 |
| CAGTCTCCCT | CCGATCTGGA | TAGCTTGGAC | GGGCGGAGCC | TTAATGATGA | TGGCAGCAGC | 120 |
| GACCCTAGGG | ATATCGACCA | GGACAACCGA | AGCACGTCCC | CCAGTATCTA | CAGCCCTGGA | 180 |
| AGTGTGGAGA | ATGACTCTGA | CTCATCTTCT | GGCCTGTCCC | AGGGCCCAGC | CCGCCCCTAC | 240 |
| CACCCACCTC | CACTCTTTCC | TCCTTCCCCT | CAACCGCCAG | ACAGCACCCC | TCGACAGCCA | 300 |
| GAGGCTAGCT | TTGAACCCCA | TCCTTCTGTG | ACACCACTG | GATATCATGC | TCCCATGGAG | 360 |
| CCCCCCACAT | CTCGAATGTT | CCAGGCTCCT | CCTGGGGCCC | CTCCCCCTCA | CCCACAGCTC | 420 |
| TATCCTGGGG | GCACTGGTGG | AGTTTTGTCT | GGACCCCCAA | TGGGTCCCAA | GGGGGAGGG | 480 |
| GCTGCCTCAT | CAGTGGGGGG | CCCTAATGGG | GGTAAGCAGC | ACCCCCCACC | CACTACTCCC | 540 |
| ATTTCAGTAT | CAAGCTCTGG | GGCTAGTGGT | GCTCCCCAA | CAAAGCCGCC | TACCACTCCA | 600 |
| GTGGGTGGTG | GGAACCTACC | TTCTGCTCCA | CCACCAGCCA | ACTTCCCCCA | TGTGACACCG | 660 |
| AACCTGCCTC | CCCCACCTGC | CCTGAGACCC | CTCAACAATG | CATCAGCCTC | TCCCCCTGGC | 720 |
| CTGGGGGCCC | AACCACTACC | TGGTCATCTG | CCCTCTCCCC | ACGCCATGGG | ACAGGGTATG | 780 |
| GGTGGACTTC | CTCCTGGCCC | AGAGAAGGGC | CCAACTCTGG | CTCCTTCACC | CCACTCTCTG | 840 |
| CCTCCTGCTT | CCTCTTCTGC | TCCAGCGCCC | CCCATGAGGT | TTCCTTATTC | ATCCTCTAGT | 900 |
| AGTAGCTCTG | CAGCAGCCTC | CTCTTCCAGT | TCTTCCTCCT | CTTCCTCTGC | CTCCCCCTTC | 960 |
| CCAGCTTCCC | AGGCATTGCC | CAGCTACCCC | CACTCTTTCC | CTCCCCCAAC | AAGCCTCTCT | 1020 |
| GTCTCCAATC | AGCCCCCCAA | GTATACTCAG | CCTTCTCTCC | CATCCCAGGC | TGTGTGGAGC | 1080 |
| CAGGGTCCCC | CACCACCTCC | TCCCTATGGC | CGCCTCTTAG | CCAACAGCAA | TGCCCATCCA | 1140 |
| GGCCCCTTCC | CTCCCTCTAC | TGGGGCCCAG | TCCACCGCCC | ACCCACCAGT | CTCAACACAT | 1200 |
| CACCATCACC | ACCAGCAACA | GCAACAGCAG | CAGCAGCAGC | AGCAGCAGCA | GCAGCATCAC | 1260 |
| GGAAACTCTG | GGCCCCCTCC | TCCTGGAGCA | TTTCCCCACC | CACTGGAGGG | CGGTAGCTCC | 1320 |
| CACCACGCAC | ACCCTTACGC | CATGTCTCCC | TCCCTGGGGT | CTCTGAGGCC | CTACCCACCA | 1380 |
| GGGCCAGCAC | ACCTGCCCCC | ACCTCACAGC | CAGGTGTCCT | ACAGCCAAGC | AGGCCCCAAT | 1440 |
| GGCCCTCCAG | TCTCTTCCTC | TTCCAACTCT | TCCTCTTCCA | CTTCTCAAGG | GTCCTACCCA | 1500 |
| TGTTCACACC | CCTCCCCTTC | CCAGGGCCCT | CAAGGGGCGC | CCTACCCTTT | CCACCGGTG | 1560 |
| CCTACGGTCA | CCACCTCTTC | GGCTACCCTT | TCCACGGTCA | TTGCCACCGT | GGCTTCCTCG | 1620 |
| CCAGCAGGCT | ACAAAACGGC | CTCCCCACCT | GGGCCCCAC | CGTACGGAAA | GAGAGCCCCG | 1680 |

| | | | | | |
|---|---|---|---|---|---|
| TCCCCGGGGG | CCTACAAGAC | AGCCACCCCA | CCCGGATACA | AACCCGGGTC | GCCTCCCTCC | 1740
| TTCCGAACGG | GGACCCCACC | GGGCTATCGA | GGAACCTCGC | CACCTGCAGG | CCCAGGGACC | 1800
| TTCAAGCCGG | GCTCGCCCAC | CGTGGGACCT | GGGCCCTGC | CACCTGCGGG | GCC | 1853

That which is claimed is:

1. A method of screening compounds for the ability to inhibit binding of GAPDH to polyglutamine, comprising the steps of:

a) providing an aqueous solution containing a test compound, molecules comprising polyglutamine, and GAPDH; and b) detecting whether binding of GAPDH to said molecules is reduced in the presence of said test compound compared to that which would occur in the absence of said test compound.

* * * * *